United States Patent
Null et al.

(10) Patent No.: US 8,298,269 B2
(45) Date of Patent: Oct. 30, 2012

(54) ORTHOPEDIC REVISION CONNECTOR (75) Inventors: William B. Null, Olive Branch, MS (US); Marc T. Paul, Memphis, TN (US); Micheal C. Sherman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/054,000

(22) Filed: Mar. 22, 2011

(65) Prior Publication Data

US 2011/0190828 A1    Aug. 4, 2011

Related U.S. Application Data (62) Division of application No. 11/583,467, filed on Oct. 18, 2006, now Pat. No. 7,976,567.

(51) Int. Cl.
*A61B 17/70* (2006.01)
(52) U.S. Cl. .......... 606/267; 606/250; 606/279
(58) Field of Classification Search ........... 606/246–279
See application file for complete search history.

(56) References Cited

U.S. PATENT DOCUMENTS

| | | | |
|---|---|---|---|
| 5,209,752 A | 5/1993 | Ashman et al. | |
| 5,282,801 A | 2/1994 | Sherman | |
| 5,527,314 A | 6/1996 | Brumfield et al. | |
| 5,545,167 A | 8/1996 | Lin | |
| 5,562,662 A * | 10/1996 | Brumfield et al. | 606/279 |
| 5,725,528 A | 3/1998 | Errico et al. | |
| 5,797,911 A | 8/1998 | Sherman | |
| 6,050,997 A * | 4/2000 | Mullane | 606/250 |
| 6,176,861 B1 | 1/2001 | Bernstein et al. | |
| 6,261,288 B1 | 7/2001 | Jackson | |
| 6,379,357 B1 | 4/2002 | Bernstein et al. | |
| 6,413,257 B1 | 7/2002 | Lin et al. | |
| 6,485,491 B1 | 11/2002 | Farris et al. | |
| 6,755,830 B2 | 6/2004 | Minflde | |
| 7,717,939 B2 * | 5/2010 | Ludwig et al. | 606/250 |
| 2006/0079892 A1 * | 4/2006 | Roychowdhury et al. | 606/61 |

FOREIGN PATENT DOCUMENTS

EP    1 269 929    1/2006

\* cited by examiner

*Primary Examiner* — Eduardo C Robert
*Assistant Examiner* — Stuart S Bray (57) ABSTRACT

A connector apparatus for use in orthopedic procedures includes a base portion and an extending leg portion that forms a channel. Part of the base portion can be placed atop or adjacent implanted fixation members (e.g. bone screws), and a locking member can be inserted through the base and into the fixation member to anchor the connector to the fixation member. A rod can be inserted into the channel and fixed to the connector by a set screw. The apparatus is useful in connecting a rod to a fixation member, particularly in situations in which a rod is already connected to the fixation member, as by a previous implantation procedure, for example.

7 Claims, 5 Drawing Sheets

ORTHOPEDIC REVISION CONNECTOR

This application is a divisional of co-pending U.S. application Ser. No. 11/583,467, filed Oct. 18, 2006, the entire contents of which are hereby incorporated by reference.

The present disclosure relates to implants useful in orthopedic surgery, and in particular to implants useful in making corrections or revisions to previously-placed implant apparatus.

In the field of orthopedic surgery, it is well-known to implant apparatus into bone and/or other tissue in order to provide support, correction, or other therapeutic benefit to tissues. For example, in the field of spinal orthopedic surgery, a set of bone screws may be implanted, one in each of a number of vertebrae, and a rod can be seated and locked in the bone screws. In this way, the rod is fixed to a plurality of vertebrae and holds the vertebrae in a particular relationship, exerts force on the vertebrae to correct their positioning, or otherwise stabilizes the vertebrae.

In some cases, such an implanted apparatus may need to be adjusted or corrected after the original implantation surgery is completed. For example, where an implantation of such apparatus occurs when a patient is relatively young, the patient's subsequent growth may require revision of the implant so as not to impede proper growth or to put corrective forces on an area or in an orientation that is different from what was originally needed. As another example, a rod-based system may be implanted in a patient needing substantial support in an area of the spine, but as time passes that magnitude of support may not be needed, or support may be needed in a different area. In those cases, an adjustment, correction or other revision of the implanted system may be undertaken in a new surgical procedure.

To this point, revision procedures generally require unlocking of bone fixation members and removal of the implanted rod, and then placement of a new rod having the new desired corrective or therapeutic attributes in the bone fixation members. In some cases, tissue can grow into or onto parts of the implant system, and thus unlocking of fixation members and/or removal of a rod can involve removal of tissue, even to injury of bone or other tissue that may be part of the healing or corrective process. Additionally, unlocking fixation members, such as pedicle or other screws, can cause damage to the fixation members themselves. In such cases, the fixation members may have to be removed and replaced, with further trauma visited upon the bone(s) and associated tissues.

There are also cases in which multiple rods or other elongated members of the same or differing size are indicated. In spinal applications, such members of different sizes may be indicated for use on the same vertebrae (e.g. substantially alongside or parallel to each other) or on adjacent vertebrae (e.g. a somewhat larger diameter rod along a set of vertebrae generally inferior and adjacent to vertebrae along which a smaller rod is placed).

Accordingly, there is a need for apparatus that can be used in revision cases to revise previously-implanted structures with less or no disruption to the adjacent tissues and less risk of damage to aspects of the previously-implanted structure that are to remain in the patient, and in initial implantation cases as well.

SUMMARY

Among other things, there is disclosed an orthopedic connector apparatus that can include a connector for connecting a head of a bone fixation member to a rod. Embodiments of such a connector can include a unitary body having a substantially planar base with a first end and a second end and an L-shaped leg offset from the base, so that the leg and the base form a channel for an orthopedic rod. The first end of the base can have a threaded first hole facing part of the leg, and the second end of the base can have a second hole, and the holes may have respective longitudinal axes that are substantially parallel. The second end of the base can be sized and configured to substantially cover the head of a bone fixation member. Additionally, a set screw may be threaded in the first hole, and a locking member inserted in the second hole, so that the locking member can be inserted in the head of the bone fixation member to lock the locking member and the apparatus to the bone fixation member.

In particular embodiments, the locking member includes a threaded shaft, and/or the leg includes a surface substantially facing the second end and having an indentation, which indentation may be substantially part-cylindrical to accommodate part of the head. The locking member may include a head that extends at least partially above the base. The apparatus may include a rod locked in the channel, with the set screw contacting the rod and pressing it against a portion of the leg. The set screw can be configured so that its top surface, when the rod is locked in the channel, is not above the base.

The disclosure also concerns an orthopedic apparatus having an implanted spinal support structure including at least one fixation member having a head with a channel and an opening transverse to the channel, with the structure also including a first rod in the channel and fixed to the head. A connector having a base with a first end and a second end and an L-shaped leg offset from the base so that the leg and base form a channel for an orthopedic rod, with the first end of the base having a threaded first hole facing part of said leg and the second end of the base having a second hole with a longitudinal axis substantially parallel to a longitudinal axis of the first hole, can be connected to the head so that the second end of the base substantially covers the head and the second hole at least partially communicates with the opening of the head. A second rod may be fixed to the connector in the connector channel. A locking member may be inserted through the second hole and into the fixation member to anchor the connector to the head. In embodiments in which the fixation member includes a set screw with an internal print in the head so that the set screw closes at least a portion of the opening, the locking member may include a threaded portion inserted into the internal print to form a threaded or interference fit. An adhering substance (e.g. cement or adhesive) can be placed between the locking member and the set screw. A set screw could be threaded through the first hole and into contact with the second rod, fixing the second rod to the connector. The connector can be made so that the second end of the base sits atop the head or so that the second hole substantially surrounds a portion of the head, and the fixation member can be one of a multi-axial bone screw, a fixed-axis bone screw, or an orthopedic hook.

Methods are also disclosed, including a method of revising a previously-implanted spinal implant apparatus that includes one or more of accessing the previously-implanted spinal implant apparatus, which apparatus has a first rod fixed to the heads of at least two fixation members; connecting a first connector to a first of the fixation member heads and a second connector to a second of the fixation member heads, each of the connectors having a base with a first end and a second end and an L-shaped leg offset from the base, the leg and base forming a channel for a second rod, the first end of the base having a threaded first hole facing part of the leg, and the second end of the base having a second hole; placing a revision rod in the connectors' channels; and locking the second rod to the connectors. Embodiments of such methods can include moving one or both of the fixation members with respect to another prior to the locking, which moving could be one of distracting, compressing or rotating one or both of the fixation members with respect to another. The connecting step may include inserting respective locking members through the second holes of the connectors and into contact with respective fixation members. Where the fixation members include respective set screws that lock the first rod, to the respective fixation members, the respective locking members may be inserted into the set screws to lock the connectors to respective fixation members. Embodiments can also include removing a piece of the first rod from between the fixation members.

Further embodiments of methods disclosed herein can include a method of implanting spinal implant apparatus that includes one or more of implanting a first fixation member having a head with a substantially U-shaped channel and an opening transverse to the channel; inserting a first rod in the channel; locking the first rod in the channel; connecting a first connector to the first fixation member head, the connector having a base with a first end and a second end and an L-shaped leg offset from the base, the leg and the base forming a channel for a second rod, the first end of the base having a threaded first hole facing part of the leg, and the second end of the base having a second hole; placing a second rod in the channel of the connector; and locking the second rod to the connectors.

DESCRIPTION OF THE ILLUSTRATED EMBODIMENTS

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein being contemplated, as would normally occur to one skilled in the art to which the disclosure relates.

Referring generally to the figures, there is shown an embodiment of a connector 20 useful in connecting elongated members, such as spinal rods, to other orthopedic implants such as bone screws or hooks, and which can be useful in orthopedic revision surgeries, initial implantations, or other procedures. As further described below, connector 20 can be connected to previously-implanted apparatus 21, such as bone screws 22, 24 that are connected to one or more rods 26.

Multiple such connectors 20 may be fixed to a revision rod 28. One or more connectors 20 may also be used in other procedures, such as initial implanting procedures in which multiple rods or elongated members of one or more sizes are used, along the same or adjacent vertebrae.

Connector 20 is a unitary or monolithic piece in the illustrated embodiment, having a substantially planar base portion 30 and an offset leg portion 32. Base 30 has a first end portion 34 generally proximate to leg 32 and a second end portion 36. Each end portion 34, 36 has a respective hole 38, 40 therethrough. Holes 38, 40 each have respective central longitudinal axes 42, 44 that in the illustrated embodiment are parallel or substantially parallel. Hole 38 in first end portion 34 is threaded in this embodiment, but may be otherwise configured. Hole 40 in second end portion 36 is also threaded in this embodiment, but in other embodiments may be substantially smooth or otherwise configured.

Leg 32 is substantially L-shaped in this embodiment, forming a channel 45 with base 30. Channel 45 communicates with hole 38. Channel 45 may be thought of as being substantially C-shaped, or the part of connector 20 associated with first end 34 and leg 32 may be thought of as a substantially C-shaped receiving end having two branches defining channel 45. If viewed in that way, second end portion 36 may be thought of as an extension from that receiving end. The surface of leg 32 that substantially faces end portion 36 includes a hollow or indentation 46 in the illustrated embodiment, which may substantially correspond to the outer profile of a bone screw or other fixation implant. In a particular embodiment, indentation 46 forms part of a cylinder. Channel 45 is dimensioned so that rods of various diameters can be carried and locked therein.

End portion 36, in the illustrated embodiment, is dimensioned so that a head portion of a fixation member, e.g. bone screws 22, 24, is substantially or completely covered or surrounded by end portion 36. In a particular embodiment, end portion 36 has a lower surface 47 that is substantially planar around hole 40, and surface 47 rests atop the head of screw 22 or other bone fixation member, so that hole 40 is adjacent an opening or a locking member in screw 22.

A set screw 48 is also provided as part of the illustrated embodiment of connector 20. Set screw 48 has a portion 50 that extends into channel 45 when set screw 48 is sufficiently threaded into hole 38. Portion 50 may have a substantially conical tip, as in the illustrated embodiment, or may be otherwise configured. Portion 50 is for contacting revision rod 28 so as to lock it to connector 20 in channel 45. An internal print 52 is provided for insertion of a tightening tool (not shown), and in the illustrated embodiment is substantially hexagonal in form.

A threaded locking member 53 having in internal driving print 54 extends through hole 40 to engage a plug 56, which in turn can connect to a bone fixation member, such as screw 22 or 24. In the illustrated embodiment, locking member 53 has a threaded shaft 58, and internal print 54 in the illustrated embodiment is substantially hexagonal in form for insertion of an appropriate tightening or holding tool (not shown). A retaining ring 60 may also be provided in hole 40 and around shaft 58 to allow locking member 53 to rotate with respect to hole 40 and perhaps ring 60, but also to prevent locking member 53 from falling out of hole 40. Ring 60 may be a split ring, a circular washer, or similar structure. Plug 56, in the illustrated embodiment, has a driving portion 62, an externally-threaded lower portion 64, and an internally-threaded opening 66. Driving portion 62 is an external hexagonal head in this embodiment, but may alternatively be square or otherwise-shaped. Threaded portion 64 is configured to be matably threaded into a fixation member (e.g. screw 22 or 24), as indicated below. Opening 66 is threaded at least part way through driving portion 62, and may extend into threaded portion 64. The threads in opening 66 are configured to accommodate threads of shaft 58 in this embodiment.

The use of the apparatus described above will now be described in certain embodiments, and in the context of spinal surgery. It is to be understood that other orthopedic surgical uses and of the apparatus described herein in other surgical contexts can be made.

Figure 1:
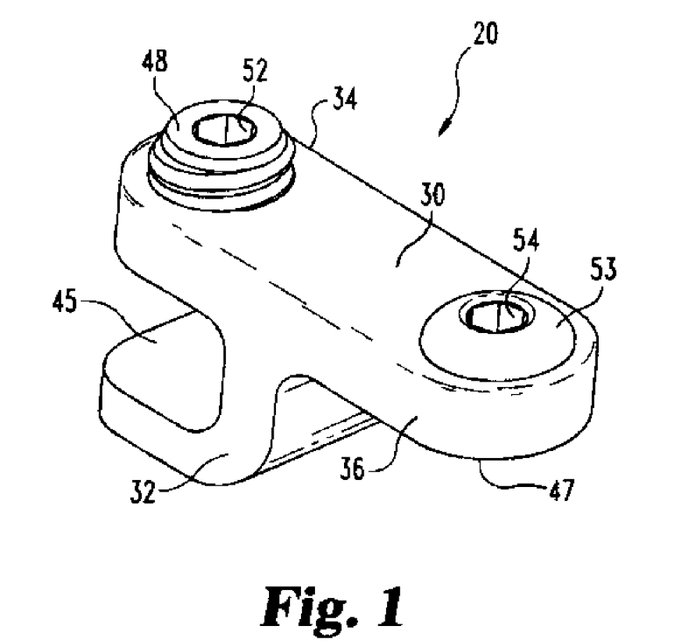
FIG. 1 is a perspective view of an embodiment of a connector apparatus.
Figure 2:
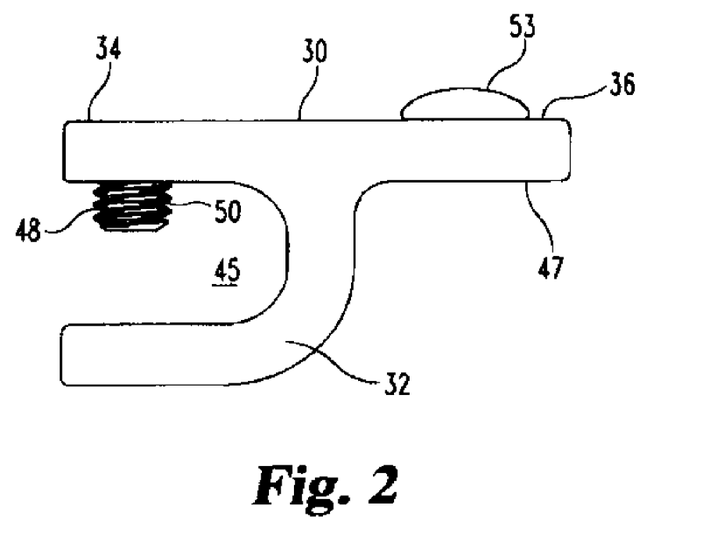
FIG. 2 is a side view of the embodiment shown in FIG. 1.
Figure 3:
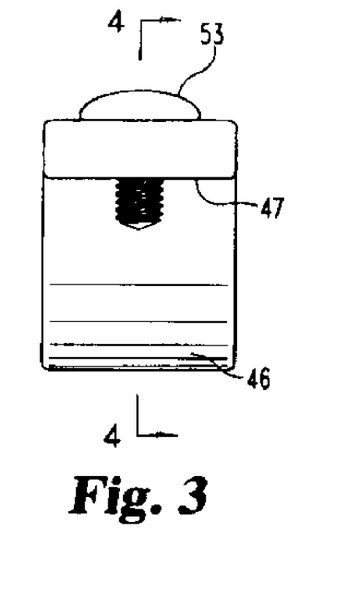
FIG. 3 is a front view of the embodiment shown in FIG. 1.
Figure 4:
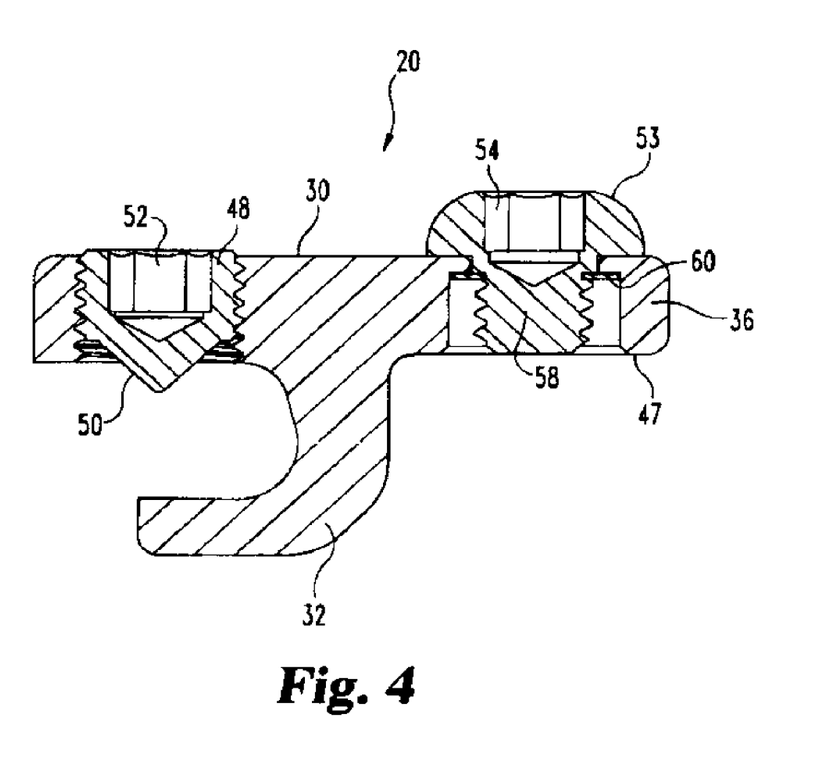
FIG. 4 is a cross-sectional view, taken along the lines IV-IV in FIG. 3 and viewed in the direction of the arrows, of aspects of the embodiment shown in FIG. 1.
Figure 5:
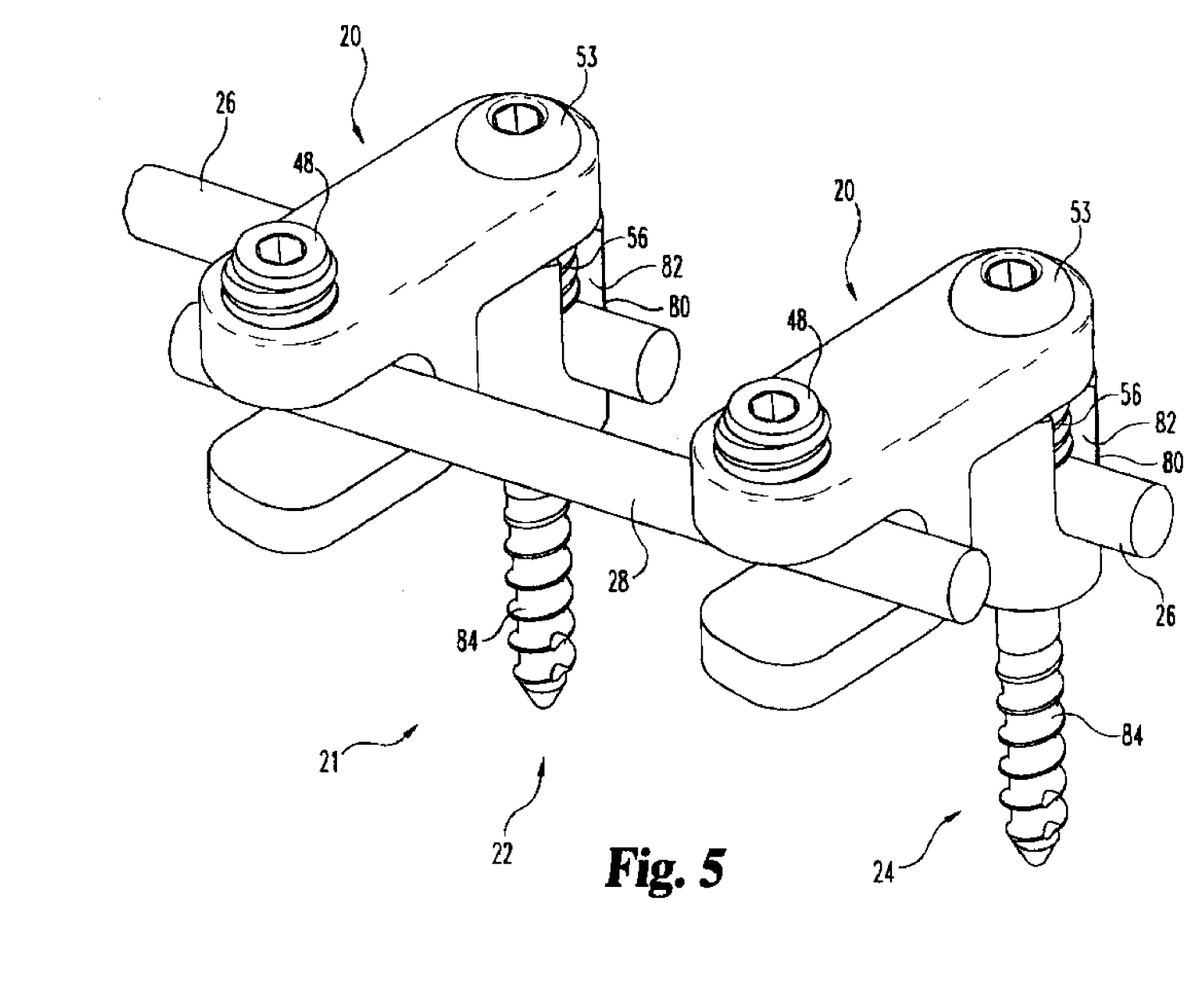
FIG. 5 is a perspective view of embodiments as shown in FIG. 1 connected to previously-implanted devices.
Figure 6:
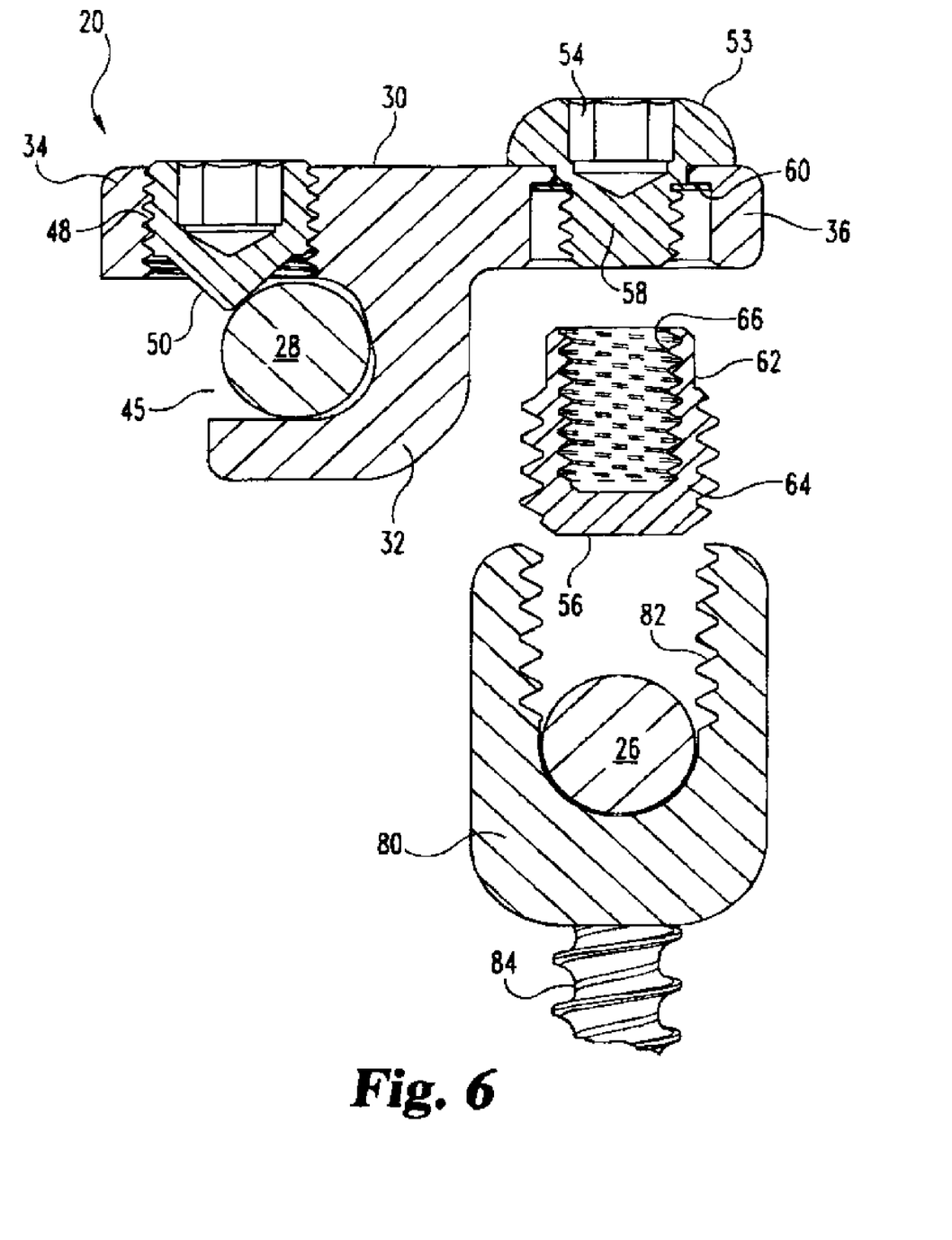
FIG. 6 is a side view with a partial cross-section of aspects as shown in FIGS. 1 and 5.

Referring generally to FIG. 5, there is represented an apparatus 21 that includes two bone screws 22, 24 between and to each of which a rod 26 is fixed. For purposes of the immediate discussion, apparatus 21 may be thought of as having been previously implanted and in need of revision. The illustrated embodiments of screws 22 and 24 are multi-axial screws, having a head portion 80 with a substantially U-shaped channel 82, a threaded shaft portion 84 for insertion into bone, and a set screw 86 threadable into head 80 and channel 82. Shaft 84 is pivotable with respect to head 80 within a cone of possible angles. Types of multi-axial screws include those shown in commonly-owned U.S. Pat. Nos. 6,280,442 and 5,797,911, both incorporated herein by reference in their entireties. Rod 26 in this embodiment is a substantially cylindrical rod. Although two screws 22, 24 are shown connected to rod 26 in the figures, it will be understood that additional screws or other fixation members or apparatus may be connected to rod 26 to the right or left (as seen in FIG. 5) of screws 22 or 24.

Where a single unitary rod 26 joins screws 22 and 24, and adjustment is needed between the vertebrae in which screws 22 and 24 are implanted, the surgeon (after obtaining access to the surgical site) may cut rod 26 and remove a portion between screws 22 and 24. When the connection between screws 22 and 24 is cut, then adjustments can take place. For example, a distractor or compressor tool (not shown) may be introduced to act against one or both of screws 22, 24 and/or one or both of the vertebrae in which they are implanted, thereby moving the vertebrae and the screws with respect to each other. Other manipulations, with or without tools, could be performed on screws 22 and/or 24 or their respective vertebra(e).

At some point before or after such manipulation(s), connectors 20 may be placed on the heads 80 of screws 22 and 24. For clarity's sake, such placement will be described with respect to screw 22, and it will be observed that placement with respect to screw 24 will be substantially or completely identical. Connector 20 is introduced to the surgical site and end portion 36 is placed atop head 80 of screw 22. Plug 56 may be initially separate from locking member 53 and threaded into screw 22, followed by placement of connector 20 over plug 56 so that shaft 58 of locking member 53 can be threaded into opening 66 of plug 56. Alternatively, plug 56 may be initially inserted into connector 20 and loosely or tightly connected to locking member 53, then connected to screw 22, e.g. by turning one or more of connector 20, plug 56 and locking member 53 with respect to screw 22. As indicated above, end portion 36 in this embodiment sits atop head 80 so that hole 40 of end 36 is adjacent channel 82 of head 80 and opening 66 of plug 56 therein. Connector 20 is anchored to head 80 via locking member 53, inserted (e.g. threaded, in this embodiment) into opening or internal thread 66 of plug 56. In certain embodiments, cements, adhesives or other adhering substances may be placed in opening 66 of plug 56 prior to insertion of locking member 53, or may otherwise be placed between locking member 53 and plug 56 so as to improve the tight connection between them. Prior to tightening locking member 53, connector 20 may be pivoted with respect to head 80 substantially around axis 44 or an axis parallel to it. Thus, channel 45 of connector 20 may be substantially parallel to channel 84 of head 80, or channels 45 and 84 may be oblique with respect to each other.

Revision rod 28 is placed in channel 45 of connector 20. Final adjustment or manipulation of one or more of screws 22, 24, their respective vertebrae, and/or connector 20 can be made with rod 28 in channel 44. When rod 28 and connector 20 are placed as the surgeon desires with respect to head 80, set screw 48 can be tightened to press rod 28 against leg 32 of connector 20, and locking member 53 can be tightened to press end 36 of connector 20 against head 80 of screw 22.

As noted, a similar or identical process may be used to connect a second connector 20 to screw 24. In the embodiment shown in FIG. 5, two such connectors 20 are connected to respective screws 22, 24, and rod 28 is fixed to each connector 20. A revision of the previously-implanted apparatus 21 can be accomplished in this way or in a similar manner with minimal effect on tissue surrounding the previously-placed implant devices.

It will be understood that the steps noted above may be taken in a variety of orders. For example, rod 28 may be loosely or tightly connected to connector(s) 20 prior to placing connector(s) 20 on screws 22 and/or 24. As another example, adjustment or manipulation of the previously-implanted apparatus can occur prior to, along with or after placement of connector(s) 20 on screws 22 and/or 24. Yet another example is that connector(s) 20 may be tightened with respect to screws 22 and/or 24 prior to introduction of rod 28 into channel(s) 45. Other variations will be appreciated.

In the example given above, the previously-implanted rod 26 is a solid continuous rod that extends between screws 22 and 24 and beyond them. In some implant structures, two rods may be initially placed, one in a generally superior position and one in a generally inferior position. This type of case may be indicated by FIG. 5, with one rod portion 26 (e.g. the one on the left in the figure) being relatively superior, and the other rod portion 26 (e.g. the one on the right in the figure) being relatively inferior. In such cases, revision of the structure may not require cutting or removal of any part of either rod. Manipulation or adjustment of vertebrae, directly or indirectly by force applied to screws 22 and/or 24, can be performed, and connectors 20 and rod 28 may be applied as indicated above to revise such a structure.

It will further be seen that connector 20 need not be restricted to use in spinal or revision procedures. For instance, in an original or initial implantation procedure, if a surgeon deems it properly indicated he or she could include connector 20. One example of such a procedure could be implanting a first fixation device (e.g. screw 22) and extending an elongated member (e.g. the left rod or rod portion 26 seen in FIG. 5) from it, connecting the elongated member to a second fixation device (not shown). Connector 20 can then be attached to screw 22, as described above, and an offset elongated member (e.g. rod or rod portion 28 seen in FIG. 5) can be attached to connector 20 as described above. In certain embodiments, such as when placing support along vertebrae that bridge different parts of the spine, adjacent elongated members may have different diameters. For example, the left portion of rod 26 (as seen in FIG. 5) may be of a relatively smaller diameter and connected to cervical or thoracic vertebrae, and rod 28 may be of a relatively larger diameter and connected to somewhat larger thoracic or lumbar vertebrae. In such embodiments, rods 26 and 28 can run along adjacent sets of vertebrae, or may run along substantially the same set of vertebrae as each other. Rod 28 can be connected to another fixation device (e.g. a screw like screw 24), another connector 20, or a variety of other orthopedic implant devices such as a bone screw, hook, staple or other device. If desired or appropriate, further connections can be made (as suggested in FIG. 5) to another screw 24 and a further rod (e.g. right rod portion 26).

A dual-rod construct with connector 20 can be used to reinforce one or more particular locations, motion segments or levels of the spine or other tissues. For example, where a tumor is removed from or a particular trauma has been suffered by adjacent vertebrae, a dual-rod construct with connector 20 as described and suggested above can be placed across and attached to such vertebrae to provide the reinforcement and support of two rods. In some cases, the two rods used may be of smaller diameter than a single rod used for support would be, in which case some rotational flexibility may be attained. Further, a dual-rod construct with one or more connectors 20 can be used with rods of differing diameter to provide different stiffness characteristics to different spinal levels. For example, a first rod (e.g. left-hand rod 26 in FIG. 5) may have a relatively smaller diameter for use with relatively smaller vertebrae or those for which less support or rigidity may be required, while a second rod (e.g. rod 28 and/or right-hand rod 26 in FIG. 5) may have a relatively larger diameter for use with relatively larger vertebrae or those for which greater support or rigidity may be required. Thus, in addition to revision of prior surgeries, the apparatus disclosed herein can be used in other types of procedures, including use in the first instance for better reinforcement or better tailoring of apparatus to a particular patient's needs.

Although screws 22 and 24 have been described above as multi-axial screws, it will be seen that they may be any of a variety of bone fixation members, including bone fixation members having substantially U-shaped channels in them. Thus, previously-implanted structure with which connector 20 may be used can include one or more fixed-axis bone screws or hooks, screws or hooks with rotatable bone-engaging portions, plates or staples with a receiving portion for a rod or other elongated member, or other similar items.

In the above-described embodiment, locking member 53 is shown as having a head that extends above the top surface of portion 30 of connector 20. It will be understood that other embodiments of locking member 53 may be used, such as one substantially or completely below the top surface of portion 30 when connector 20 is locked to an implant, particularly if portion 30 includes a hollow or countersunk portion to accommodate some or all of a head, or if locking member 53 lacks such a head.

Figure 7:
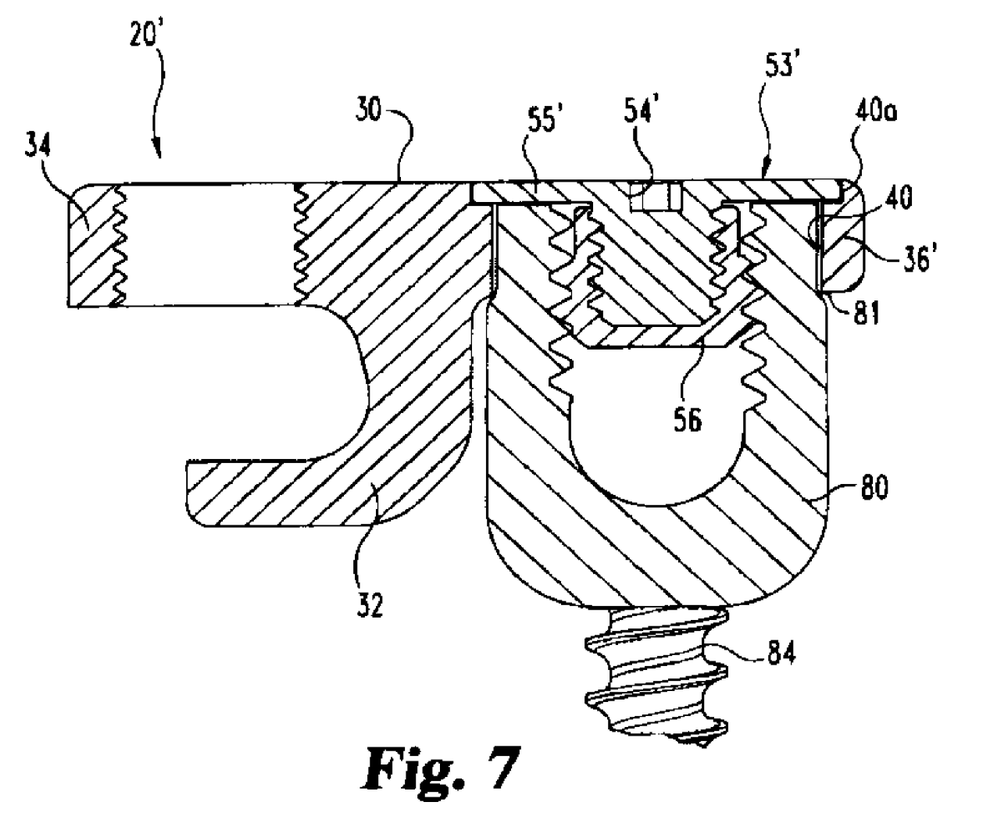
FIG. 7 is a cross-sectional view of an embodiment of a connector apparatus.

One example of such an embodiment is shown in FIG. 7. Connector 20' is generally the same as connector 20 in most respects, and thus the same numbers are used to indicate similar features. However, in this embodiment hole 40 of connector 20' is large enough to be placed around screw head 80, akin to a ring around the head, and a ledge or countersunk surface 40a is provided around hole 40. A locking member 53' is provided with a broad, relatively flat head 55' in the illustrated embodiment, which is joined to a threaded shaft 53' and includes an internal driving print 54' (shown hexagonal as one example).

In use, connector 20' fits over screw head 80, as indicated above, in situations identical and similar to those described herein for use of connector 20. Screw head 80 is inserted in hole 40 of connector 20' until it is just below the top surface of connector 20'. In the illustrated embodiment, screw head 80 has an outwardly sloping or conical medial portion 81, and connector 20' forms an interference fit with portion 81, preventing connector 20' from sliding further down head 80. End 36' of connector 20' is of a thickness such that the top surface of connector 20' is slightly above the top of screw head 80, in this embodiment. Locking member 53' is threaded into plug 56 in screw head 80, and head 55' of locking member 53' abuts the top of screw head 80 and ledge 40a in connector 20'. Tightening locking member 53' locks it against ledge 40a, head 80 and plug 56, preventing connector 20' from lifting away from head 80. Thus, this embodiment of connector 20' provides the advantages of connector 20, with an even lower profile.

While the disclosure has been illustrated and described in detail in the drawings and foregoing description, the same is to be considered as illustrative and not restrictive in character, it being understood that all changes and modifications that come within the spirit of the disclosure are desired to be protected. For example, a locking member such as locking member 53 could be inserted directly into a set screw already within a channel of a fixation member such as screw 22 or 24, and in such constructs a separate plug 56 is not needed. As discussed above, the connection between such a locking member and an existing set screw could be threaded, enhanced by cements, adhesives or other substances, or otherwise configured.

Directional terms used herein, such as "above," "below" or similar terms, are not intended to be necessarily indicative of the orientation of the described feature in all situations. Rather, they are used in conjunction with the figures to indicate general relationships between or among features.

What is claimed is:

1. A method of revising a previously-implanted spinal implant apparatus, comprising:
    accessing the previously-implanted spinal implant apparatus, said apparatus having a first rod fixed to the heads of at least two fixation members;
    connecting a first connector to a first of said fixation member heads and a
    second connector to a second of said fixation member heads, each of said connectors having a substantially planar base with a first end portion and a second end portion and an L-shaped leg offset from said base, said leg and said base forming a second channel configured for receipt of a second rod, said first end portion of said base having a threaded first hole facing part of said leg, said second end portion of said base having a second hole, said holes having respective longitudinal axes that are substantially parallel, wherein said second end portion of said base substantially covers said head of said bone fixation member;
    placing the second rod in said channels of said connectors:
    placing a set screw into the first hole;
    inserting a locking member into the second hole to lock said second rod to said connectors, wherein said locking member is engaged with said head of said bone fixation member to lock said locking member and said connector body to said bone fixation member; and wherein said leg includes a surface substantially facing said second end portion, said surface having an indentation and wherein said indentation is substantially part-cylindrical to accommodate part of said head of said bone fixation member.

2. The method of claim 1, further comprising moving one or both of said fixation members with respect to another prior to said locking.

3. The method of claim 2, wherein said moving is one of distracting, compressing or rotating one or both of said fixation member with respect to another.

4. The method of claim 1, wherein said connecting step includes inserting respective locking members through said second holes of said connectors and into contact with respective said fixation members.

5. The method of claim 4, wherein said respective fixation members each include a set screw that locks said first rod to the respective fixation members, and said respective locking members are inserted into said set screws to lock said respective connectors to said respective fixation members.

6. The method of claim 1, further comprising removing a piece of said first rod from between said fixation members.

7. A method of implanting spinal implant apparatus, comprising:
- implanting a first fixation member, said fixation member having a head with a substantially U-shaped channel and an opening transverse to said channel;
- inserting a first rod in said channel;
- locking said first rod in said channel;
- connecting a first connector to said first fixation member head, said connector having a substantially planar base with a first end portion and a second end portion and an L-shaped leg offset from said base, said leg and said base forming a second channel configured for receipt of a second rod, said first end portion of said base having a threaded first hole facing part of said leg, said second end portion of said base having a second hole, said holes having respective longitudinal axes that are substantially parallel, wherein said second end portion of said base substantially covers said head of said bone fixation member;
- placing the second rod in said channel of said connector;
- placing a set screw into the first hole;
- inserting a locking member into the second hole to lock said second rod to said connectors, wherein said locking member is engaged with said head of said bone fixation member to lock said locking member and said connector body to said bone fixation member; and
- wherein said leg includes a surface substantially facing said second end portion, said surface having an indentation and wherein said indentation is substantially part-cylindrical to accommodate part of said head of said bone fixation member.

* * * * *